(12) United States Patent
Shoham

(10) Patent No.: US 8,469,963 B2
(45) Date of Patent: Jun. 25, 2013

(54) BONE DRILLING CANNULA

(75) Inventor: Moshe Shoham, Hoshaya (IL)

(73) Assignee: Mazor Robotics Ltd., Caesarea (IL)

( * ) Notice: Subject to any disclaimer, the term of this patent is extended or adjusted under 35 U.S.C. 154(b) by 857 days.

(21) Appl. No.: 12/042,072

(22) Filed: Mar. 4, 2008

(65) Prior Publication Data
US 2008/0221581 A1   Sep. 11, 2008

Related U.S. Application Data

(60) Provisional application No. 60/904,798, filed on Mar. 5, 2007.

(51) Int. Cl.
*A61B 17/60* (2006.01)
*A61F 2/00* (2006.01)
*A61M 5/178* (2006.01)

(52) U.S. Cl.
USPC ........................................ 606/96; 604/164.09

(58) Field of Classification Search
USPC .................. 604/164.01, 164.09, 164.11, 264; 606/96–97, 183, 185, 186
See application file for complete search history.

(56) References Cited

U.S. PATENT DOCUMENTS

| | | |
|---|---|---|
| 5,139,500 A | 8/1992 | Schwartz |
| 5,403,322 A | 4/1995 | Herzenberg et al. |
| 5,458,602 A | 10/1995 | Goble et al. |
| 5,571,133 A * | 11/1996 | Yoon .............................. 606/185 |
| 6,238,355 B1 * | 5/2001 | Daum ............................ 600/567 |
| 6,293,925 B1 * | 9/2001 | Safabash et al. .............. 604/136 |
| 6,416,518 B1 | 7/2002 | DeMayo |
| 6,607,530 B1 | 8/2003 | Carl et al. |
| 6,761,726 B1 * | 7/2004 | Findlay et al. ................. 606/182 |
| 7,033,363 B2 | 4/2006 | Powell |
| 7,060,068 B2 | 6/2006 | Tromanhauser et al. |
| 7,691,086 B2 * | 4/2010 | Tkebuchava ............. 604/164.01 |

FOREIGN PATENT DOCUMENTS

CA       2524127       12/1994

* cited by examiner

*Primary Examiner* — Anu Ramana
(74) *Attorney, Agent, or Firm* — Fish & Richardson P.C.

(57) ABSTRACT

A drilling guide cannula, having a serrated distal end in the form of axially moveable teeth which enables all or most of the teeth to maintain biting contact with the bone surface, essentially independently of the curvature of the bone surface and the drilling angle. The cannula outer wall incorporates a number of pins arranged circumferentially around the drilling bore. These pins slide axially relative to the cannula, preferably in bored holes or in channels formed within the wall of the cannula. Each of the secondary pins has a sharpened distal end, each constituting a moveable tooth. The cannula is applied to the bone to be drilled at the desired drilling position and angle, and the pins are forced axially towards the bone surface. The pins take up the contour of the bone surface and each pin bites into the bone surface to rigidly position the drilling guide cannula.

16 Claims, 5 Drawing Sheets

SECTION C-C

BONE DRILLING CANNULA

FIELD OF THE INVENTION

The present invention relates to the field of devices for enabling accurate drilling in orthopaedic surgical procedures, especially for drilling into a bone at angles away from the normal to the bone surface.

BACKGROUND OF THE INVENTION

In many orthopaedic surgical procedures, there is need to drill holes in the bone of the patient, in order to insert fixation devices or surgical inserts. Surgical screws are widely used in orthopedic surgery to fix broken bones as well as to maintain the broken bones in alignment during the healing process. The hole for receiving these inserts or fixation devices are generally prepared by drilling through a cannulated drill guide, and many such drill guides have been described in the prior art.

In U.S. Pat. No. 5,403,322 to J. E. Herzenberg et al, for "Drill guide and method for avoiding intramedullary nails in the placement of bone pins", there is described a drill sleeve or a guide-wire sleeve having a toothed or serrated distal end, such that the sleeve bites into the bone into which the drilling is being performed, and constitutes a firm guide for the drill. In this patent, there is a description of how the surgeon inserts the guide wire sleeve through the drill sleeve until the serrated distal end touches the bone. He then strikes the guide wire sleeve proximal end, causing the teeth or serrations to be imbedded (i.e., bite) into the bone. In this invention, the sleeve is not used on its own, but is the fourth rigid fixation point of a four-bar construction, thus rendering the drilling position highly stable. As stated in this patent, "(t)his resulting construct thus attains the stability required to prevent the guide wire, drill bit, or bone pin from walking or skiving off the side of the slippery, rounded contour of bone, known to be a problem without the stability attained with the four-bar construct as above-described."

In U.S. Pat. No. 6,607,530 to A. Carl et al., there is described in FIG. 3A a drill guide sleeve having at its distal end a plurality of fixed teeth that bite into the bony surface of a vertebra to assist in preventing slipping of the drill guide.

In U.S. Pat. No. 7,060,068 to S. G. Tromanhauser et al., for "Vertebrae fastener placement guide", there is described another composite guide system construction having two guiding members each of which has a bone-engaging surface with serrations to minimize slippage of the guide against the bone.

However, in many cases, such a rigid structure is not used, and the drilling guide is instead used solo, often hand held, such as in U.S. Pat. No. 6,416,518 to E. N. DeMayo for "Combined surgical drill and surgical screw guide". In such use, the above mentioned problem of skiving off the bone can be significant. When used on a reasonably flat bone surface, and at normal or close to normal incidence to the bone, many or even all of the teeth or serrations on the end of the sleeve grip the bone surface together, thus providing non-slipping functionality to the drill guide. However, when the hole has to be drilled into a small diameter bone having a distinctly curved outer surface, or even when the hole is to be drilled in a flat bone surface, but at a significant angle of incidence to the bone surface, it is likely that only a small number of the teeth or serrations at the end of the guide sleeve will contact the bone, and there is then danger that the guide sleeve will slip during use, rendering the hole position inaccurate.

There therefore exists a need for a surgical drilling guide which can be used independently of a larger drilling and guiding construction, and which nevertheless provides a rigid drilling positioning, thus overcoming at least some of the disadvantages of prior art guides.

The disclosures of each of the publications mentioned in this section and in other sections of the specification, are hereby incorporated by reference, each in its entirety.

SUMMARY OF THE INVENTION

The present invention seeks to provide a new surgical drilling guide cannula, having a serrated distal end in the form of sharpened teeth for providing firm contact with the bone surface to be drilled, and which enables all or most of the teeth to maintain biting contact with the bone surface, essentially independently of the curvature of the bone surface, and essentially independently of the required drilling angle. The drilling guide cannula of the present invention comprises a bore through which the drilling is performed. The cannula outer wall preferably has a thickness sufficient to incorporate a number of secondary pins arranged circumferentially around the drilling bore. These pins slide axially relative to the cannula, preferably in bored holes formed within the wall of the cannula, or in channels formed therein. Each of the secondary pins has a sharpened distal end. The cannula is applied to the bone to be drilled, at the desired drilling position and angle, and the secondary pins are forced axially towards the bone surface. This forcing action is preferably performed by the action of tapping the pins at their proximal ends, such that each moves distally until contact is made with the bone surface. By this means the pins take up the contour of the bone surface at the drilling point, and each pin, regardless of where it is circumferentially located, bites firmly into the bone surface to rigidly position the drilling guide assembly. A locking collar is preferably provided to ensure that the position of the pins is maintained when lateral forces may be applied to the cannula during the drilling process. The pins can also be forced into contact with the bone profile by other methods, such as by the application of spring pressure, or by use of hydraulic pressure to force them towards the bone surface.

There is therefore provided in accordance with a preferred embodiment of the present invention, a guiding cannula comprising:
(i) a cylindrical guide tube having an inner bore down which a surgical tool may be inserted, the tube having a distal end for application to the surface of a bone of a subject,
(ii) a plurality of axially moveable pins disposed around the inner bore and externally thereto, each of the pins having a sharp end disposed at the distal end of the guide tube, such that when the pins are pushed axially in a distal direction, each of the sharp ends protrudes beyond the distal end of the guide tube, and
(iii) a locking device to lock the axial positions of the pins.

In such a guiding cannula, the sharp ends protruding beyond the distal end of the guide tube are preferably adapted to contact the bone surface. Furthermore, the pins preferably move independently of each other, may be disposed circumferentially around the inner bore, and may move within axial passages in the wall of the guide tube.

In accordance with yet more preferred embodiments of the present invention, in the above-described guiding cannula, the locking device may be a conically matched pair of collars, or it may be hydraulically pressurized.

Furthermore, In accordance with further preferred embodiments of the present invention, essentially all of the pins, when extended in a distal direction, may be adapted to make firm contact with the bone surface independently of the angle at which the cannula is applied to the bone. Additionally and preferably, essentially all of the pins, when extended in a distal direction, may be adapted to make firm contact with the bone surface independently of the surface profile of the bone.

There is even further provided in accordance with more preferred embodiments of the present invention, a guiding cannula as described above, further comprising a spring loaded pushing device for applying an axial force on the pins, or further comprising a hydraulically actuated pushing device for applying an axial force on the pins, or further comprising a pushing device constructed of a pliable material for applying an axial force on the pins. Any of these pushing devices are preferably such that the axial force is applied to each of the pins independently.

BRIEF DESCRIPTION OF THE DRAWINGS

The present invention will be understood and appreciated more fully from the following detailed description, taken in conjunction with the drawings in which:

FIG. 3 shows how the teeth of the cannula of FIG. 2 are moved axially to conform to the surface profile of the bone being operated on;

DETAILED DESCRIPTION OF PREFERRED EMBODIMENTS

Figure 1:
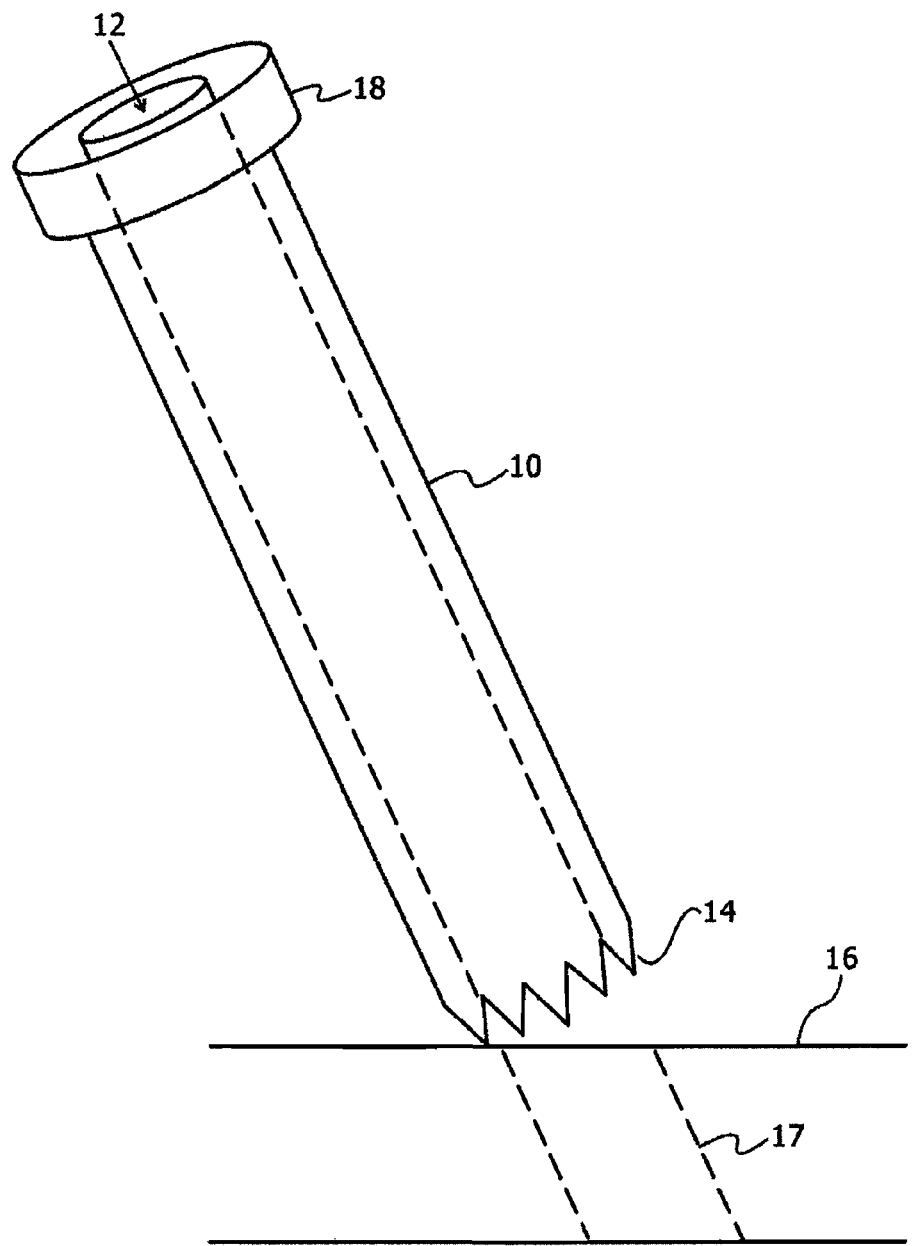
FIG. 1 shows a prior art drill guide, having fixed teeth for gripping the bone.

Reference is now made to FIG. 1, which illustrates schematically a prior art drill guide, such as is described in some of the references cited hereinabove. The drill guide 10 has a bore 12 through which the drill or other surgical tool is inserted and guided. At its distal end, the drill guide has a number of circumferentially disposed teeth, generating a serrated edge 14. At its proximal end, the guide preferably has a knurled knob 18 for gripping the guide, or for pushing or striking it, so that the teeth bite into the bone to be operated on, thereby providing positional stability to the guide. In FIG. 1, the guide is shown being applied to the bone 16 of a subject at the angle required to drill the hole 17 desired. Because this angle is not normal to the surface of the bone, and also because of the small diameter of the bone, only a small number of the teeth of the serrated edge, or even just a single tooth, may be in contact with the bone, biting into it to provide positional support and alignment rigidity for the guide. Most of the teeth remain dis-functional, as they remain suspended in the soft tissue surrounding the bone, and do not grip the bone. In these situations, such prior art drill guides with static teeth are thus prone to skiving off the bone when forces are applied during the drilling process.

Figure 2:
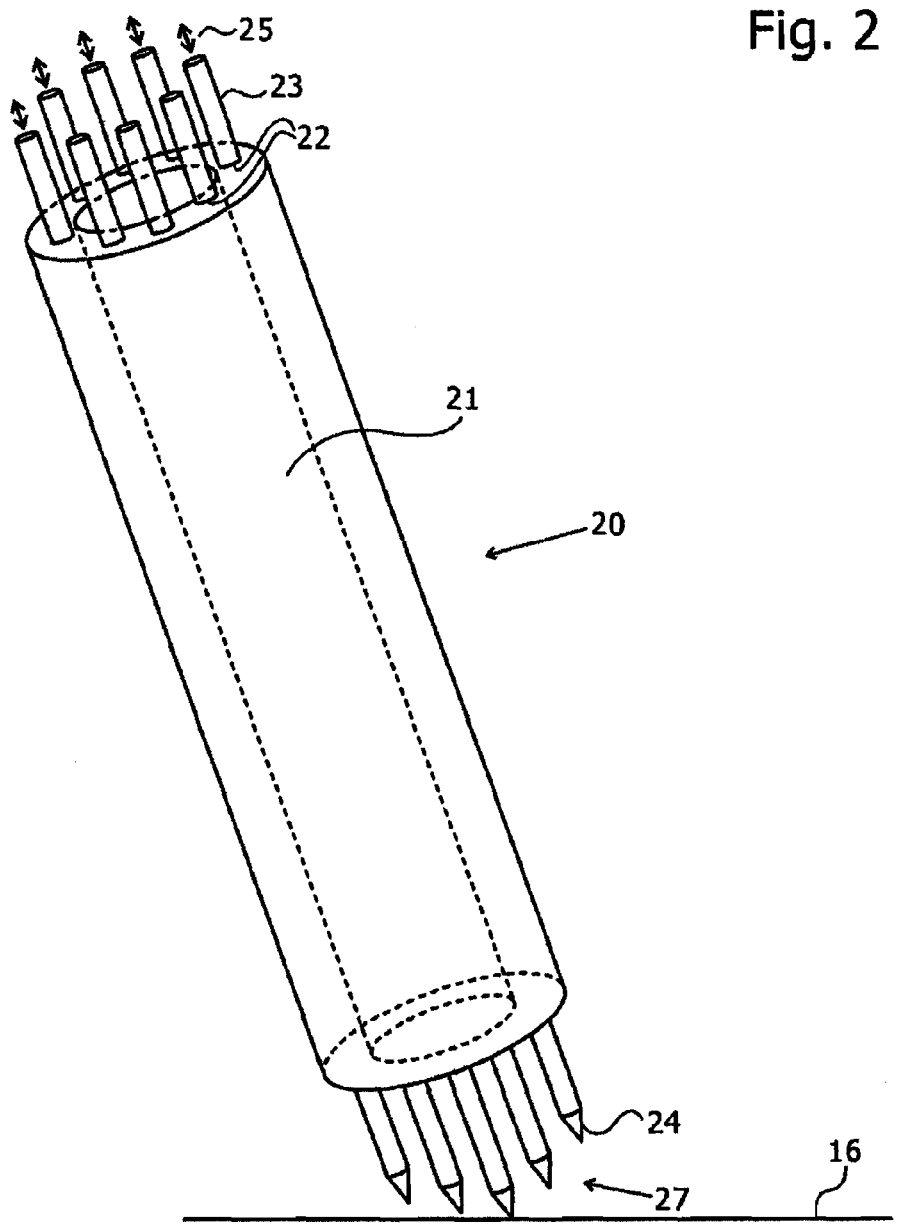
FIG. 2 is an isometric schematic illustration of a drill guide cannula, constructed and operative according to a first preferred embodiment of the present invention, showing the pins in their unextended positions.

Reference is now made to FIG. 2, which is a schematic isometric illustration showing a cannula 20 for use as a drill guide, constructed and operative according to a first preferred embodiment of the present invention. The guiding cannula 20 comprises a hollow tube, whose central bore 21 is adapted to take the drill or other surgical tool it is desired to guide. Within the wall of the cannula are a number of axial bores 22, positioned preferably equi-spaced around the circumference of the guide cannula. Through each of these bores is inserted a sharpened pin or thin rod 23, which is a sliding fit within its bore, such that each pin can move axially 25 up and down its bore. The sharpened ends 24 of the pins are directed towards the distal end of the cannula. The proximal ends of the pins protrude from the proximal end of the guide cannula. The distal end of the cannula resembles that of the prior art cannula of FIG. 1, in that it has a circumferential array of teeth 27 for gripping the bone to which it is applied.

Figure 3:
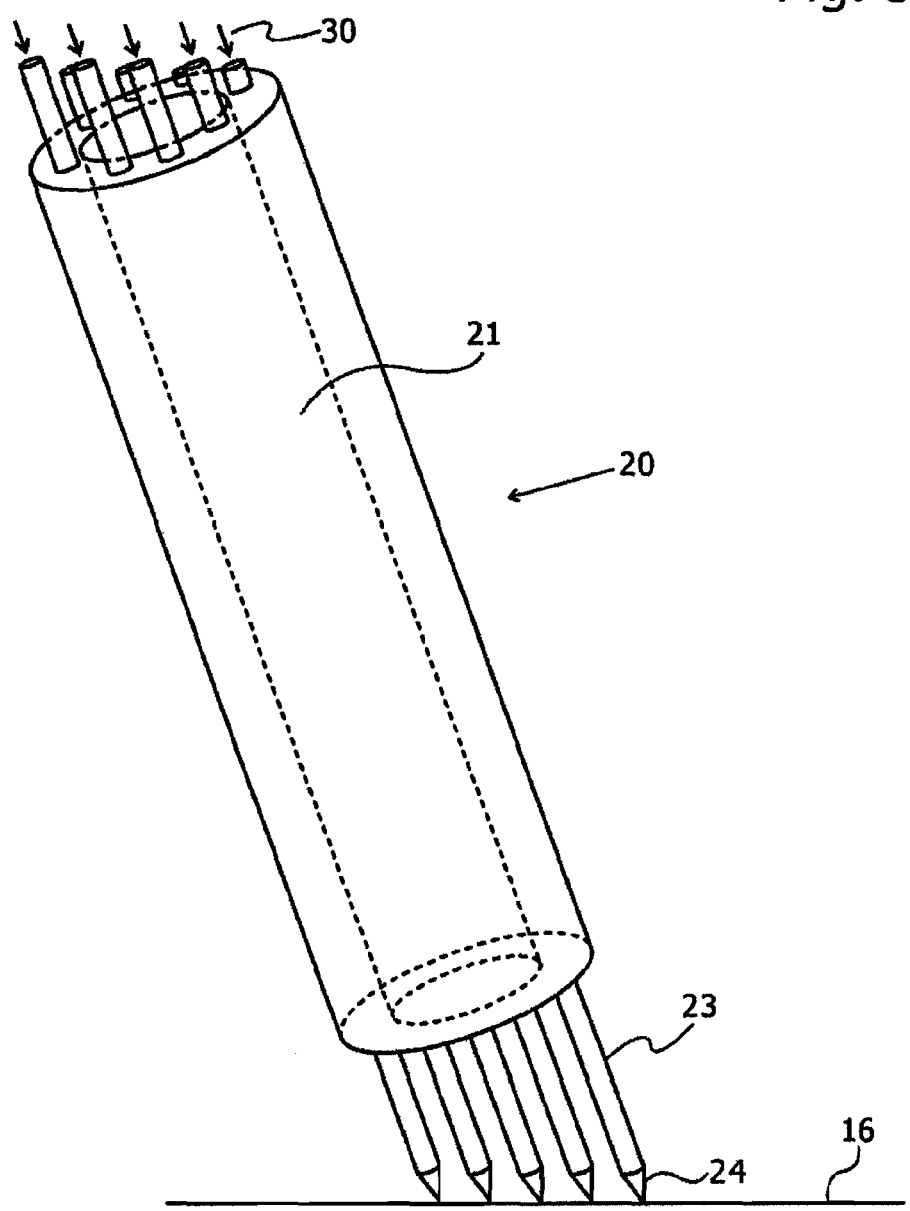

Reference is now made to FIG. 3, which illustrates schematically how, as a result of this sliding pin structure, the operation of the cannula 20 of the present invention provides significant advantages over the prior art cannula of FIG. 1. The axial movement of the pins 23 enables the "teeth" 24 to move to conform to the surface profile of the bone 16 being operated on, such that all of the teeth can make contact with, and bite into the bone. In practice, this function is achieved by forcing all of the pins from their proximal end in a distal direction 30, each independently of the others, until the sharpened end 24 of each comes into contact with the bone surface 16.

A mechanism is preferably provided for pushing all of the pins independently in an axial direction, or the pins may simply be tapped into position one at a time using a small surgical hammer. A further mechanism, such as a friction conical lock nut, is preferably provided for locking the pins in position once they have conformed to the bone surface profile. Once the pins are locked in place, the desired hole can be drilled with the confidence that the drill guide firmly grips the bone using all or almost all of the teeth of the device, thus providing a significant advantage over prior art drilling guides.

In the preferred embodiments of FIGS. 2 and 3, the bores of the pins are shown as separate drillings within the outer wall of the cannula. It is to be understood that the invention is not meant to be limited by this preferred structure for holding the pins in their intended circumferential positions, and that any alternative method, such as machined channels or slots, or a cage structure to hold the pins in place around the inner bore, could equally well be used in implementing the invention.

Figure 4:
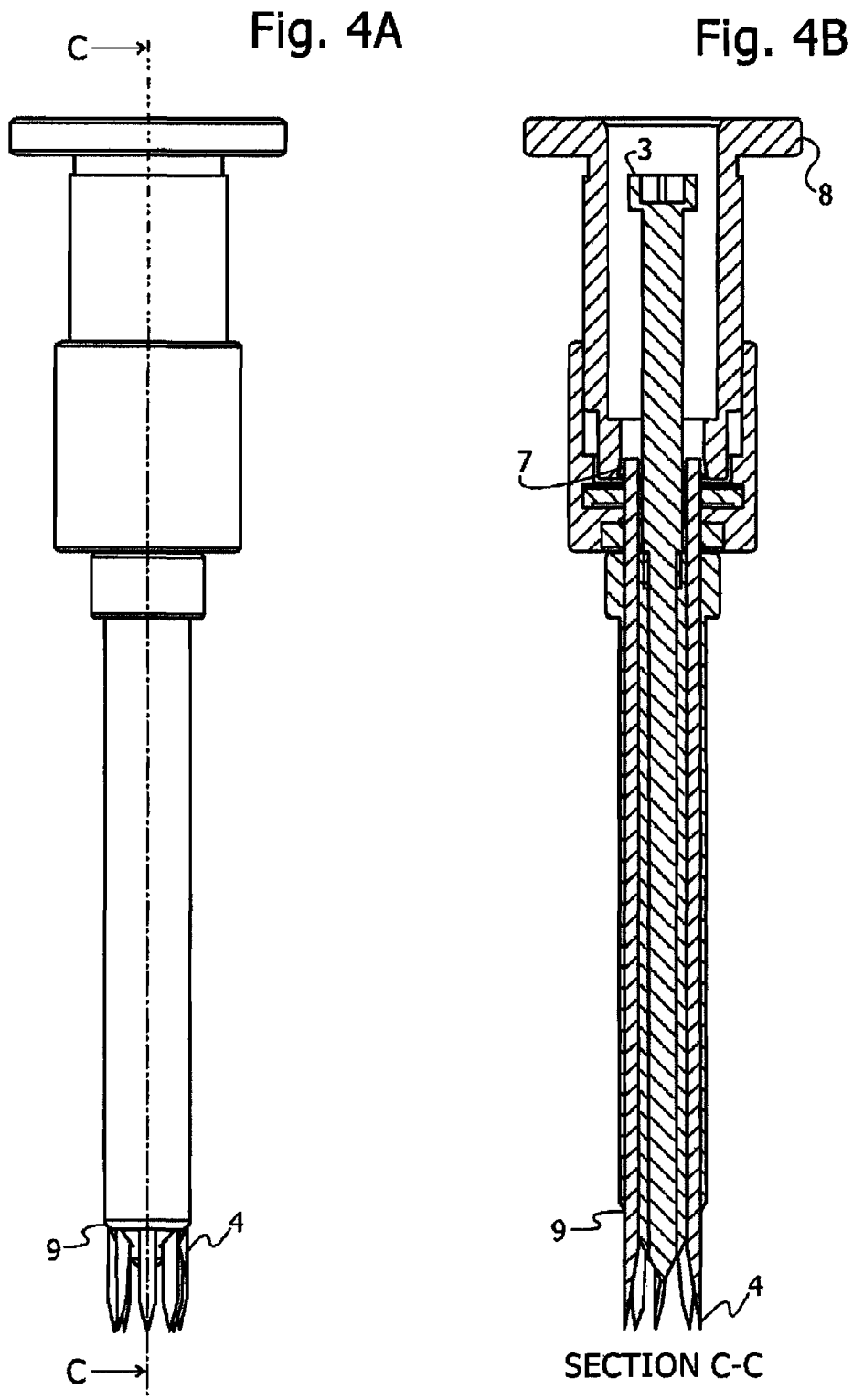
FIGS. 4A and 4B are schematic drawings showing a mechanical pushing and locking mechanism for use with the cannulae of FIGS. 2 and 3, to lock the pins into their intended positions.

Reference is now made to FIGS. 4A and 4B, which are engineering assembly drawings of one preferred embodiment of the guide cannula, showing respectively an external and a cross-sectional view. In this embodiment, the pins 4 are locked into place by means of a matching cone device 7, once their mutual protrusion from the cannula barrel wall 9 has been adjusted to conform to the bone profile. Their position is obtained by pushing down on plunger 3, which has a distal shoulder made of a flexible material, such that the shoulder can push each pin to its own position against the bone profile. A mechanical collar is fitted onto the neck of the cannula where the proximal ends of the pins protrude. The collar has a conical neck 7, into which fits an annular element having a matching conical outer surface, and whose inner surface contacts the pins. When the collar is tightened, by means of a threaded locking ring 8, the annular locking element is contracted radially inwards, like the action of a collet, and the pins are gripped in the position to which they have been pushed. The plunger 3 can then be withdrawn to enable the drilling to be performed.

Figure 5:
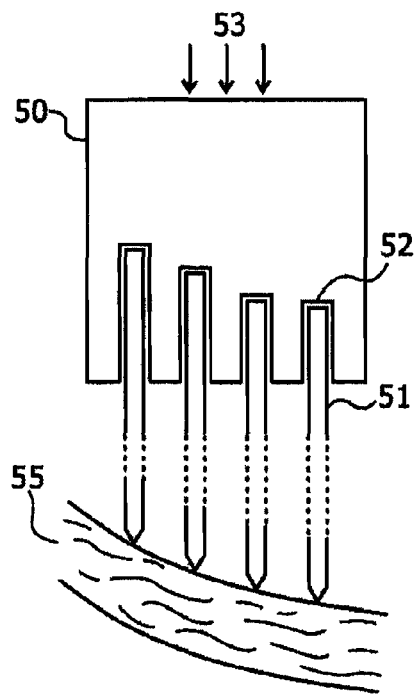
FIG. 5 is a schematic drawing of a plug constructed of a pliable material, for exerting axial pressure on the pins of the embodiments of FIGS. 2 and 3.
Figure 6:
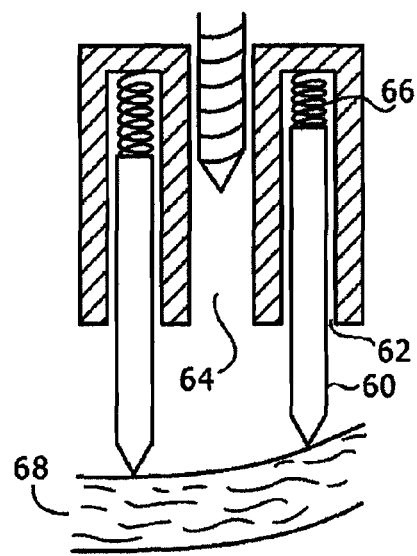
FIG. 6 is a schematic drawing of a spring loaded pushing mechanism for use with the cannulae of FIGS. 2 and 3, to extend the pins to their intended positions.
Figure 7:
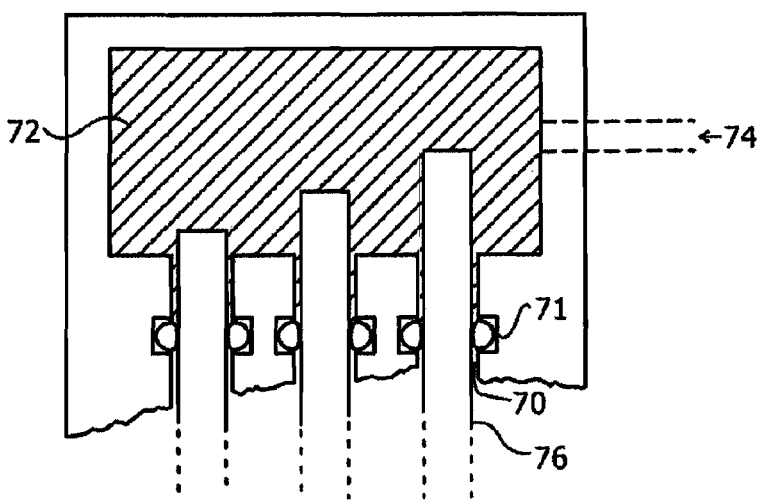
FIG. 7 is a schematic drawing of a hydraulic system for ensuring that the pins are extended to and locked in their intended positions.

Reference is now made to FIGS. 5 to 7, which illustrate several different preferred embodiments of the present invention, by which the pins are fixed into the position dictated by the bone surface profile onto which the drilling cannula is forced.

FIG. 5 schematically illustrates a preferred embodiment in which the pins are forced axially into their extended position and held in place there, by use of a plug 50 constructed of a pliable material, such as a rubber material, which has a central bore for the drilling channel (not shown), and which sits in the proximal part of the drilling cannula. This plug applies pressure to all of the pins 51 when pressed down upon them, but its level of pliability enables each pin to compress the material to a different extent, according to the pin's final position against the bone surface, such that all of the pins are held in their different extended positions by the compressibility of the plug. The plug may preferably have blind holes, in each of which one pin sits, with the unstrained depth of all the holes being as shown for hole 52. Each pin sits in its associated hole at the same height before pressure is applied to the plug. Pressure 53 on the plug causes each pin to compress the pliable material at the base of its hole to the extent required by its pin's final rest position against the profile of the bone surface. As shown in the example of FIG. 5, the pins on the left of the drawing of the plug have compressed the material behind the base of their hole more than those on the right, because of the profile of the bone 55.

According to further preferred embodiments of the present invention, the pins can be held in their desired protruding positions by means of mechanical springs, which exert an axial force in a distal direction on each of the pins separately. Such an embodiment is shown schematically in FIG. 6, which shows a cross-sectional view. Each of the pins 60 slides within a bore 62 having a blanked off proximal end, with a pressure spring 66 contained within the bore between its blanked-off end and the end of the pin. The springs thus hold the pins in a forced extended position, and when the device is pushed against the bone 68 on which it is being used, each of the pins compresses its own spring to the extent necessary to maintain the pin in positive forced contact with the bone 68. The central bore 64 of the cannula is used as a drill guide, with the drilling cannula held firmly against the bone surface by the pressure of the springs.

According to a further preferred embodiment of the present invention, as illustrated schematically in FIG. 7, hydraulic pressure can be used to ensure that the pins are extended to their desired protruding positions, and maintained in these positions. The embodiment of FIG. 7 shows the hydraulic operating head of such a drilling cannula (central drilling channel not shown to simplify the drawing). The pins 76 slide in pin bores 70, hydraulically sealed preferably by means of O-rings 71, and connected to a reservoir 72. According to a first preferred embodiment, hydraulic pressure is applied externally from a source of pressure 74, thus ensuring that all of the pins have a positive force applied to them in their distal direction. According to a second preferred embodiment, the reservoir is a closed volume, with all of the proximal ends of the pin bores connected together as one common closed hydraulic chamber, such that the proximal retraction of any pin must be accompanied by the distal extension of another pin. As a result, when external mechanical pressure is applied to push the cannula down onto a bone, all of the pins take up their optimal positions in contact with the bone profile, and the common hydraulic reservoir pressure maintains positive pressurized contact for every pin in the array. A pneumatic reservoir can alternatively be used, this providing an element of springiness to the pin positions.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

I claim:

1. A guiding cannula comprising:
   a cylindrical guide tube having an inner bore down which a surgical tool may be inserted, said tube having a distal end adapted for biting into the surface of a bone of a subject such that said cannula is rigidly positioned;
   a plurality of axially moveable straight pins disposed around said inner bore and externally thereto, each of said pins having a sharp end pointed in the axial direction and disposed at said distal end of said guide tube, said pins with their sharp ends being moveable axially in a distal direction to a position at which each of said sharp ends protrudes in the axial direction beyond said distal end of said guide tube, said straight pins remaining straight when protruding from said guide tube; and
   a locking device to lock the axial positions of said pins.

2. A guiding cannula according to claim 1, wherein said sharp ends protruding beyond said distal end of said guide tube are adapted to make biting contact with said bone surface.

3. A guiding cannula according to claim 1, wherein said pins move independently of each other.

4. A guiding cannula according to claim 1, wherein said pins are disposed circumferentially around said inner bore.

5. A guiding cannula according to claim 1, wherein said pins move within axial passages in the wall of said guide tube.

6. A guiding cannula according to claim 1, wherein said locking device is a conically matched pair of collars.

7. A guiding cannula according to claim 1, wherein said locking device is hydraulically pressurized.

8. A guiding cannula according to claim 1, wherein essentially all of said pins, when extended in a distal direction, are adapted to make biting contact with said bone surface independently of the angle at which said cannula is applied to said bone.

9. A guiding cannula according to claim 8, said biting contact with said bone surface being such that said guiding cannula is rigidly positioned.

10. A guiding cannula according to claim 1, wherein essentially all of said pins, when extended in a distal direction, are adapted to make biting contact with said bone surface independently of the surface profile of said bone.

11. A guiding cannula according to claim 1, further comprising a spring loaded pushing device for applying an axial force on said pins.

12. A guiding cannula according to claim 11 and wherein said pushing device is such that said axial force is applied to each of said pins independently.

13. A guiding cannula according to claim 1, further comprising a hydraulically actuated pushing device for applying an axial force on said pins.

14. A guiding cannula according to claim 13 and wherein said pushing device is such that said axial force is applied to each of said pins independently.

15. A guiding cannula according to claim 1, further comprising a pushing device constructed of a pliable material for applying an axial force on said pins.

16. A guiding cannula according to claim 15 and wherein said pushing device is such that said axial force is applied to each of said pins independently.

* * * * *